US005562345A

United States Patent [19]
Heyman et al.

[11] Patent Number: 5,562,345
[45] Date of Patent: Oct. 8, 1996

[54] METHOD AND APPARATUS FOR THERMOGRAPHICALLY AND QUANTITATIVELY ANALYZING A STRUCTURE FOR DISBONDS AND/OR INCLUSIONS

[75] Inventors: Joseph S. Heyman; William P. Winfree, both of Williamsburg; K. Elliott Cramer, Newport News; Joseph N. Zalamedia, Williamsburg, all of Va.

[73] Assignee: The United States of America as represented by the Administrator of the National Aeronautics and Space Administration, Washington, D.C.

[21] Appl. No.: 571,688

[22] Filed: Dec. 13, 1995

Related U.S. Application Data

[63] Continuation of Ser. No. 878,631, May 5, 1992, abandoned.

[51] Int. Cl.$^6$ .................................................. G01N 25/72
[52] U.S. Cl. .................................................. 374/5; 374/124
[58] Field of Search .......................... 374/4, 5, 7, 124, 374/137

[56] References Cited

U.S. PATENT DOCUMENTS

| | | | |
|---|---|---|---|
| Re. 32,166 | 6/1986 | Berge | 374/5 |
| 2,587,705 | 3/1952 | De Forest | 374/5 |
| 3,629,584 | 12/1971 | Blomgren, Jr. | 374/5 |
| 3,681,970 | 8/1972 | Wells | 374/5 |
| 4,019,364 | 4/1977 | Maddox | 374/5 |
| 4,109,508 | 8/1978 | Fukuyama | 374/5 |
| 4,309,901 | 1/1982 | Rolinski et al. | 374/29 X |
| 4,439,049 | 3/1984 | Hoogendoorn et al. | 374/5 |
| 4,644,162 | 2/1987 | Bantel et al. | 374/5 |
| 4,647,220 | 3/1987 | Adams et al. | |
| 4,854,162 | 8/1989 | Yerace et al. | 374/4 |
| 4,854,724 | 8/1989 | Adams et al. | |
| 4,928,254 | 5/1990 | Knudsen et al. | |
| 4,933,887 | 5/1990 | Danko et al. | |
| 4,950,990 | 8/1990 | Moulder et al. | |
| 4,999,499 | 3/1991 | Bhatt | 374/5 X |
| 5,052,816 | 10/1991 | Nakamura et al. | 374/5 |
| 5,131,758 | 7/1992 | Heyman et al. | 374/5 |
| 5,246,291 | 9/1993 | Lebeau et al. | 374/124 |
| 5,250,809 | 10/1993 | Nakata et al. | 374/5 |

OTHER PUBLICATIONS

N. Karasikov and M. B. Roitberg, "Thermodynamic considerations for pyrelectric detectors", *Ferroelectrics*, vol. 33, 1981, pp. 217–222.

W. N. Reynolds, "Thermographic methods applied to materials", *Canadian J. Phys.*, vol. 64, No. 9, Sep. 1986, pp. 1150–1154.

W. P. Winfree, C. S. Welch, P. H. James, and E. Cramer, "Thermographic detection of delaminations in laminated structures", Review of Progress in Quantitative NDE, vol. 8B, 1989, pp. 1657–1662.

W. P. Winfree, P. A. Howell and Elliot Cramer, "Thermographic imaging of disbonds in laminated structures", ISA, 1990, Paper No. 90–181, pp. 811–816.

R. P. Bruno, "Thermography in nondestructive industrial testing", Photonics Spectra, 1989, pp. 123–126.

Microwatt Applications Brochure, Pyroelectric Infrared Sensor Series PPF–1 Single Element Device (with Integral Amp) description, 1989.

Analog Devices Brochure, Ultralow–Noise Precision Op Amp AD Op-27 description 1990.

(List continued on next page.)

*Primary Examiner*—Diego F. F. Gutierrez
*Attorney, Agent, or Firm*—Robin W. Edwards

[57] ABSTRACT

A heat source such as a magnetic induction/eddy current generator remotely heats a region of a surface of a test structure to a desired depth. For example, the frequency of the heating source can be varied to heat to the desired depth. A thermal sensor senses temperature changes in the heated region as a function of time. A computer compares these sensed temperature changes with calibration standards of a similar sample having known disbond and/or inclusion geography(ies) to analyze the test structure. A plurality of sensors can be arranged linearly to sense vector heat flow.

8 Claims, 7 Drawing Sheets

OTHER PUBLICATIONS

K. E. Cramer, W. P. Winfree, and C. S. Welch, "A handheld thermographic system for the detection of disbonds in laminated structures", ISA, 1991, unnumbered (8 pages).

W. P. Winfree and P. H. James, "Thermographic detection of disbonds", ISA, 1989, Paper 89-0017, pp. 183-188.

A. B. Shapiro, "TOPAZ2D: A two-dimensional finite element code for heat transfer analysis, electrostatics and magnetostatics problem", Lawrence Livermore Lab., 1986. (Document photocopied from microfilm and is best copy available).

P. H. James, C. S. Welch, W. P. Winfree, "A numerical grid generation scheme for thermal simulations in laminated structures", Review of Progress in Quantitative Nondestructive Evaluation, (Plenum Pub Conf, NY), pp. 801-809 1989.

J. W. Maclachlan Spicer, "Measurement of coating physical properties and detection of coating disbonds by time-resolved infrared radiometry", Journal of NDE, vol. 8, pp. 107-120, 1989.

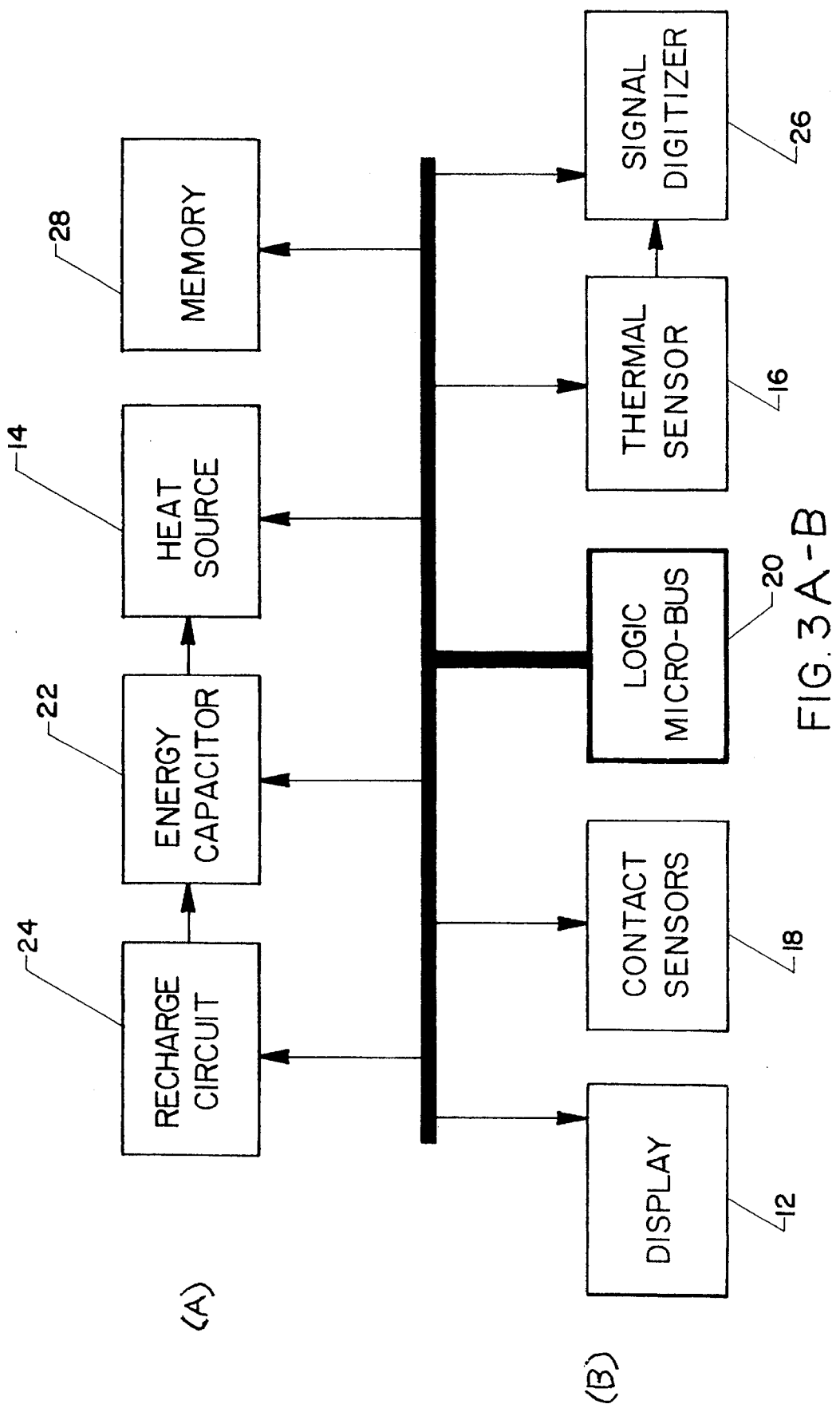
FIG. 3A-B

METHOD AND APPARATUS FOR THERMOGRAPHICALLY AND QUANTITATIVELY ANALYZING A STRUCTURE FOR DISBONDS AND/OR INCLUSIONS

Origin of the Invention

The invention described herein was made by employees of the United States Government and may be used by or for the Government for governmental purposes without the payment of any royalties thereon or therefor.

This is a continuation of application Ser. No. 07/878,631 filed on May 5, 1992, now abandoned.

BACKGROUND OF THE INVENTION

1. Technical Field of the Invention

The present invention relates generally to the nondestructive evaluation of thermal properties and more particularly to a method and apparatus for quantitatively and thermographically analyzing a structure for disbonds and/or inclusions.

2. Description of the Prior Art

The use of laminated structures in aerospace applications has increased in recent years. It has been demonstrated that thermographic techniques such as laser scanners, infrared (IR) cameras and contact temperature sensors such as thermocouples for inspection of these structures for disbonds has significant advantage in portability, expense and adaptability to field use compared to other methods. Many of these thermal techniques use full field noncontacting imaging and accordingly require a significant amount of equipment, making the inspection limited to areas of easy access. Many of the test structures currently in use are located in a somewhat inaccessible area, or their geometry is such that it is impractical to attempt to use a full field IR imager for inspection.

U.S. Pat. Nos. 4,647,220 and 4,854,724 to Adams et al disclose IR analysis of corrosion spots and spot welds. The test area is heated with a pulsed IR heat input and problem areas identified after cooling as localized hot spots, i.e., a relative measure is obtained with respect to surrounding areas rather than a quantitative value related to thermal properties over time. The technique of Adams et al is unable to recognize imperfections which encompass the entire heated area since it relies on a comparative determination.

U.S. Pat. No. 4,950,990 to Moulder et al discloses a system for photoinductive imaging for material flaw detection. A laser heats a specified area of the material and a probe detects the resulting eddy currents which are indicative of flaws or holes.

OBJECTS OF THE INVENTION

It is accordingly an object of the present invention to detect disbonds in a laminated or composite structure.

It is another object of the present invention to detect disbonds in a laminated or composite structure quantitatively.

It is another object of the present invention to differentiate between various inclusions in a laminated or composite structure.

It is a further object of the present invention to differentiate between various inclusions in a laminated or composite structure quantitatively.

It is a further object of the present invention to accomplish the foregoing objects for relatively inaccessible laminated or composite structures.

Other objects and advantages of the present invention are apparent from the specification and drawings which follow.

SUMMARY OF THE INVENTION

The foregoing and additional objects are obtained by a method and apparatus according to the present invention. A heat source such as a magnetic induction/eddy current generator remotely heats a region of a surface of a test structure to a desired depth. For example, the frequency of the heating source can be varied to heat to the desired depth. A thermal sensor senses temperature changes in the heated region as a function of time. A computer compares these sensed temperature changes with calibration standards of a similar sample having known disbond and/or inclusion geography(ies) to analyze the test structure. A plurality of sensors can be arranged lineady to sense vector heat flow.

BRIEF DESCRIPTION OF THE DRAWINGS

FIG. 3a is a block diagram of the thermograph disbond detection system of FIG. 1;

FIG. 3b is a block diagram of the computer used in FIG. 3a;

DETAILED DESCRIPTION

Figure 1:
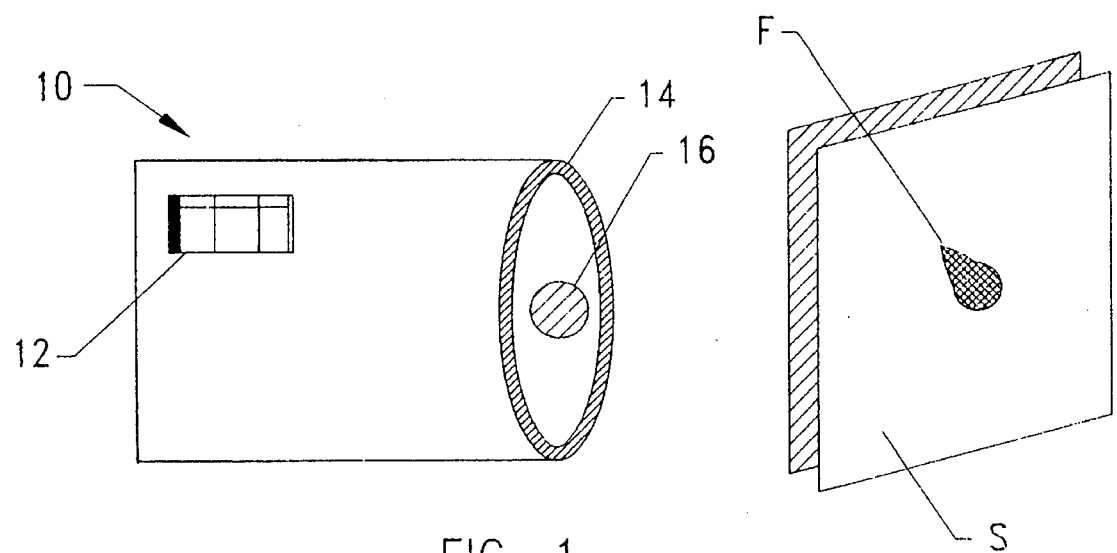
FIG. 1 is a side view of a thermographic disbond detection system according to the present invention.

The present invention is shown in reference to FIG. 1, wherein a thermographic disbond detection system analyzes 10 a sample S containing a flaw F. The detection system presents a quantitative digital display 12 of the effective thermal properties of the sample as discussed below. Heat is injected into the sample by the heating source 14 and is detected by the thermal sensor 16.

Figure 2:
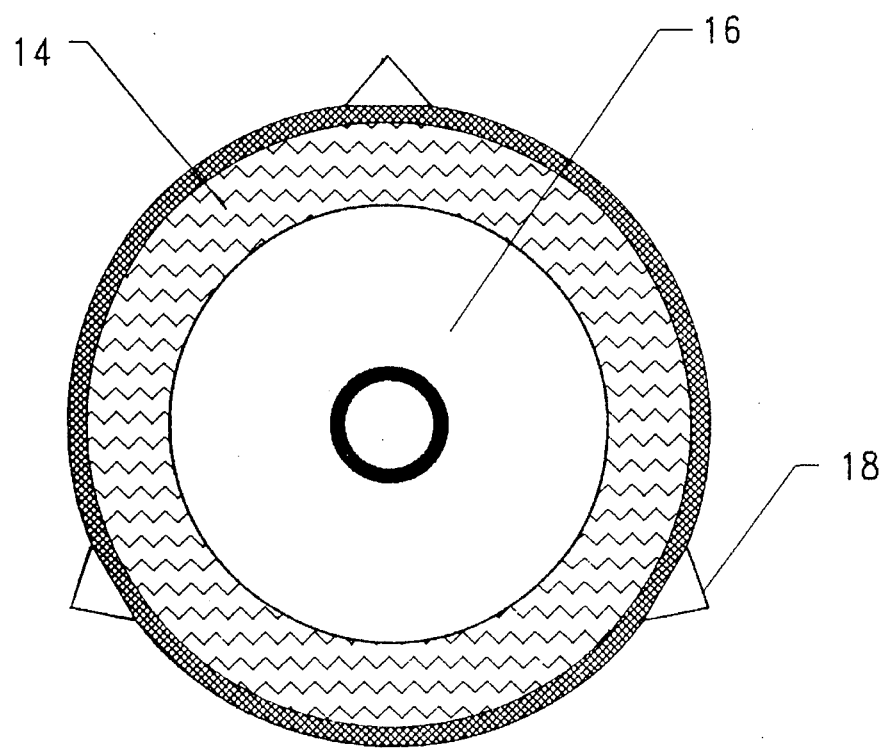
FIG. 2 is a front view of the thermographic disbond detection system of FIG. 1.
Figure 4A:
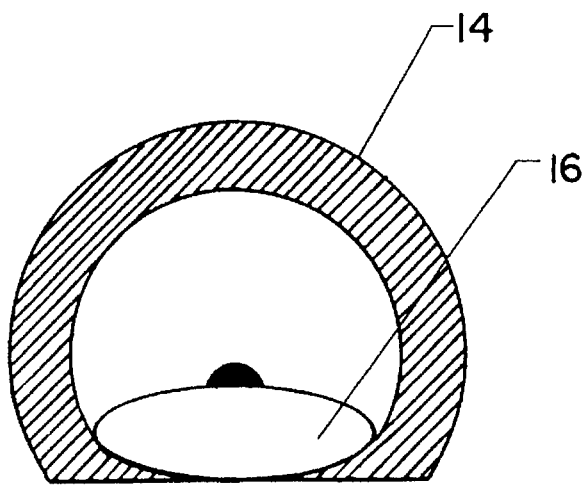
FIG. 4a is an exposed side view of a magnetic induction heating source used in the disbond detection system of FIG. 1.
Figure 4B:
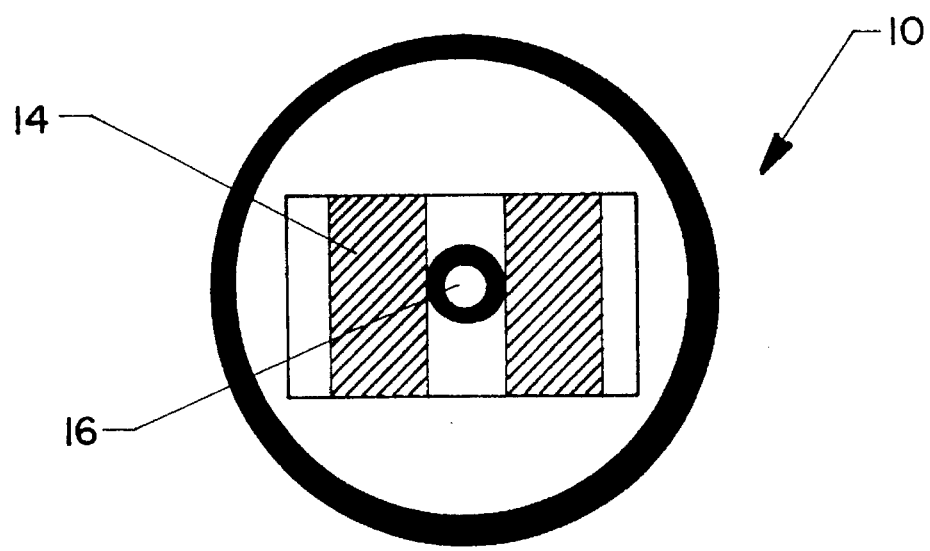
FIG. 4b is a front view of FIG. 3.

FIG. 2 shows a detail of the front of detection system consisting of the heat source 14, thermal sensor 16 and three individual contact sensors 18. For example, the thermal sensor for the detection is a thin film, pyroelectric detector such as the Model PPF-110 available from Microwatt Applications. The detector element is made of polyvinylidene fluodde ($PVF_2$) and is 1.0 mm in diameter. This detector contains a low noise FET impedance matching preamplifier within the element housing. The bandwidth for the spectral response of the detector is limited to the 8–14 micron wavelength range by an AR coated filter/window. The output of the thermal sensor 16 is then amplified with a simple, two-stage buffered (not shown) constructed using ultralow-noise precision operation amplifiers such as Model AD OP-27 available from Analog Devices. This amplifier provides a signal gain of 100. Further, a 0.1 to 45 Hz bandpass filter (not shown) was incorporated into the second state of the amplifier to eliminate any DC offset and drift and to help reduce high frequency noise. This configuration forms a detector circuit and provides a noise floor for the output signal of ±20 mV with a dynamic signal range of ±13 V. The thermal sensor 16 was positioned so that its field of view was restricted to a small region, e.g., approximately 6 mm in diameter, in the center of the heating area. Alternatively, the thermal sensor is an IR detector.

The block diagram in FIG. 3a outlines the operation of the system. A logic 20 and a connecting bus 23 of a computer or microprocessor 21 shown in FIG. 3 controls the entire system and through the bus 23 communicates to all the system parts. The sequence is started by firing a charged energy capacitor 22 in response to a computer 25 command from logic 20 to drive the heat source 14, which can be a flash tube having a rapid discharge. The energy capacitor 22 is recharged by a recharge circuit 24. The result of the discharge is to heat the sample which is measured by the thermal sensor 16. The signal produced by the detector is digitized by the signal digitizer 26 and stored in memory 28 of the computer. The output of the detector was digitized for analysis and archival by the personal computer 21 and a 12 bit analog-to-digital converter board which allowed for data collection at rates up to 142 KHz.

The heating source 14 can be a magnetic inductance device or eddy current heater, wherein the energy lost in the sample through eddy currents heats the sample region. The eddy current heater was constructed from a horseshoe-shaped ferrite core wrapped with transformer wire and driven by an RF power amplifier. An associated power amplifier (not shown) was modulated at the resonant frequency of the wrapped core coupled to the sample. This frequency was determined through manual tuning of the system to provide maximum power input into the sample. The inductive device can be of variable frequency so as to heat the near surface at a high frequency or the bulk at low frequency to differentiate the thermal properties of the bulk or the surface of the tested sample. For example, at 1 MHz, the skin depth in iron is about 0.02 mm while at 10 KHz, the depth is ~0.2 mm. The heating source 14 can be controlled by the microprocessor 21 to allow for synchronization between the start of heating and the start of data collection.

The center frequency of the magnetic source is determined by the resonance of the magnetic heating source 14, when coupled to the output of the energy capacitive source or driver 22, as a LC resonator governed by: $f=1/(2\pi \sqrt{(LC)})$, where f is the resonance frequency, L is the inductance and C the capacitance. The resonance circuit can be driven for a number of cycles as a tone burst, or can be pulse excited.

The capacitive recharge circuit 24 can switch to different capacitors to vary the resonance frequency. With this technique, one can perform a first measurement at high frequency heating only at the near surface. The radiated energy just after the excitation is a measure of the emissivity of the surface for a calibration factor. For high frequencies the material thermal properties have the appearance of extending to infinity. The surface temperature of the material is related to the emissivity of the sample, the input flux and the thermal conductivity of the sample. This factor is a normalizing constant which appears in all subsequent analytical representations of the temperature. A second heating at a lower frequency results in a measurement of the interior of the material.

The thermal sensor 16 can be alternatively radiometric based on bolometers or photon statistics, or can be contact based on any of the many temperature sensors such as thermoelectric effect, optical fiber sensors or junction electronic devices.

Figure 5:
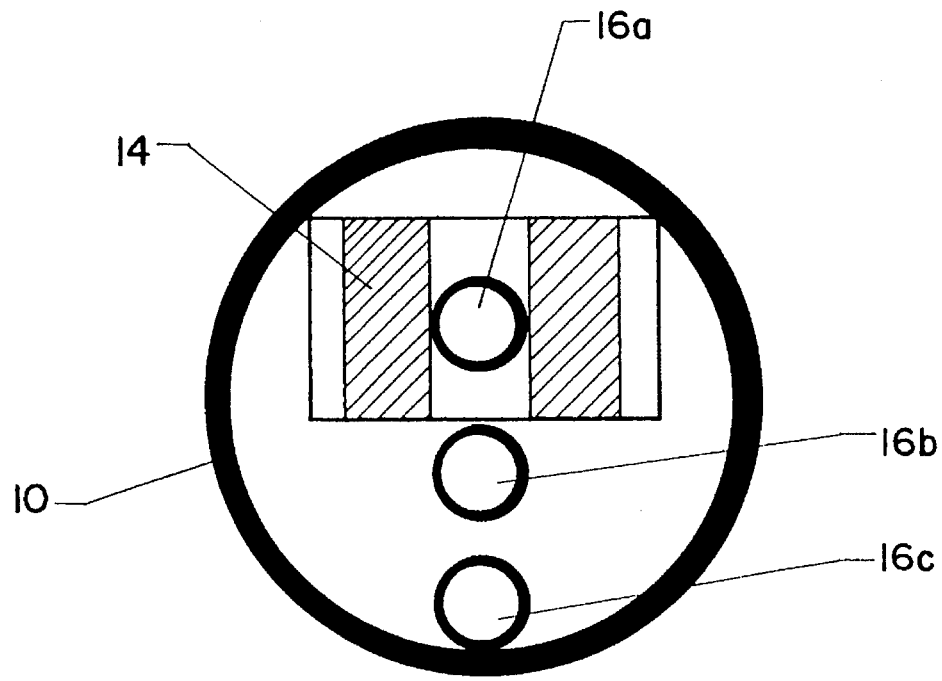
FIG. 5 is a front view of the disbond detection system using three linearly arranged thermal sensors.
Figure 6:
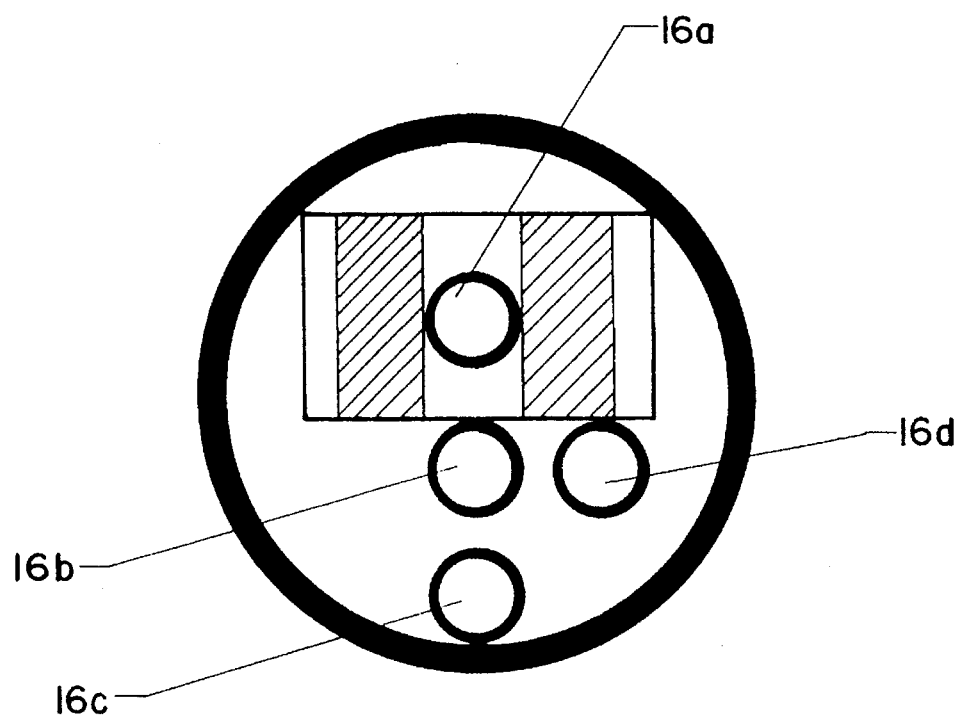
FIG. 6 is a front view of the disbond detection system using the three sensor arrangement of FIG. 5 plus an additional thermal sensor.

More than one sensor can be set into the front of the detector 10 as is shown in FIG. 5. The thermal sensors are indicated by 16a, 16b, and 16c. These three sensors permit a measurement of the vector flow of heat from the central heating source out to the periphery of the detector 10, i.e., the outermost thermal sensor. The measurement of the vector heat flow in the material enables a determination of the diffusivity tensor in the material. By comparison of the different components of the diffusivity tensor important parameters such as fiber direction or fiber volume fraction in graphite fiber reinforced composites is possible. The detector is rotated to indicate diffusion anistropy in the sample as is found in composite materials. The detector 10 is self-aligning via the three contact sensors 18 which permit the detector 10, and particularly thermal sensor 16, to be repeatably positioned with respect to the sample S. The detector 10 determines vector heat flow through a linear pattern of sensors or a two-dimensional pattern such as shown in FIG. 6. Three thermal sensors 16a, 16b, and 16c are arranged in a line and a fourth thermal sensor 16d is arranged non-linearly. In the specific embodiment depicted, fourth thermal sensor 16d is arranged linearly with the center sensor 16b of the three sensors along a line perpendicular to the line of the three sensors.

The operation of the present invention will now be discussed in greater detail. A steel-rubber-aluminum laminate sample S was fabricated with a known defect or flaw F in an inner layer. The sample consisted of a sheet of steel 0.16 cm thick, backed by a layer of rubber which was 0.63 cm thick, which was backed by a layer of aluminum 2.54 cm thick. The entire sample was 19.0 cm square. The layers were bonded together with a slow curing two-part epoxy. A disbond was produced by removing a known portion of the middle rubber layer before assembly of the sample.

Figure 7:
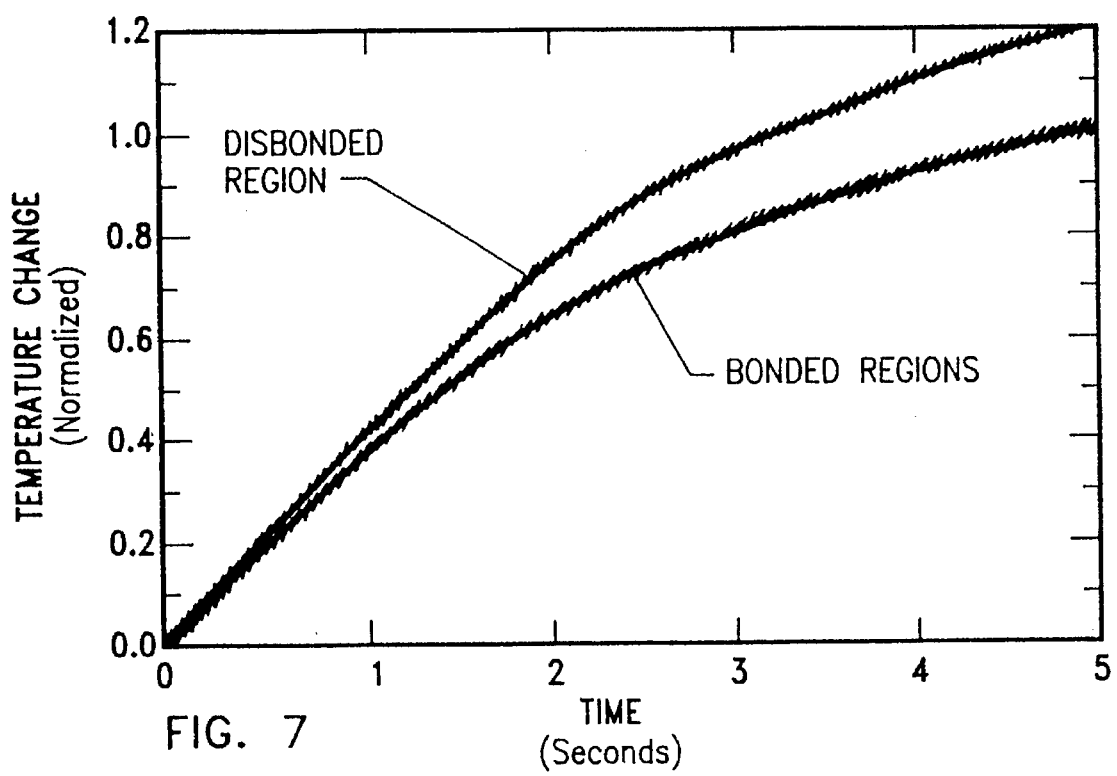
FIG. 7 graphs the normalized temperature change over time for a steel-rubber-aluminum laminate sample with a disbond region and a bonded region.

In a "two-step" measurement process, the sample was heated for five seconds using an eddy current or magnetic induction heating source 14. The heating was then discontinued and data representing temperature as a function of time was collected for approximately five seconds at a rate of 1.7 KHz via the pyroelectric thermal sensor 16 and every twenty consecutive data points were averaged to increase the signal-to-noise ratio. These "two-step" measurements were first performed over a bonded region, then the sample was repositioned so that the detector and heater were over a disbonded region. FIG. 7 shows the results of this data collection.

Figure 8:
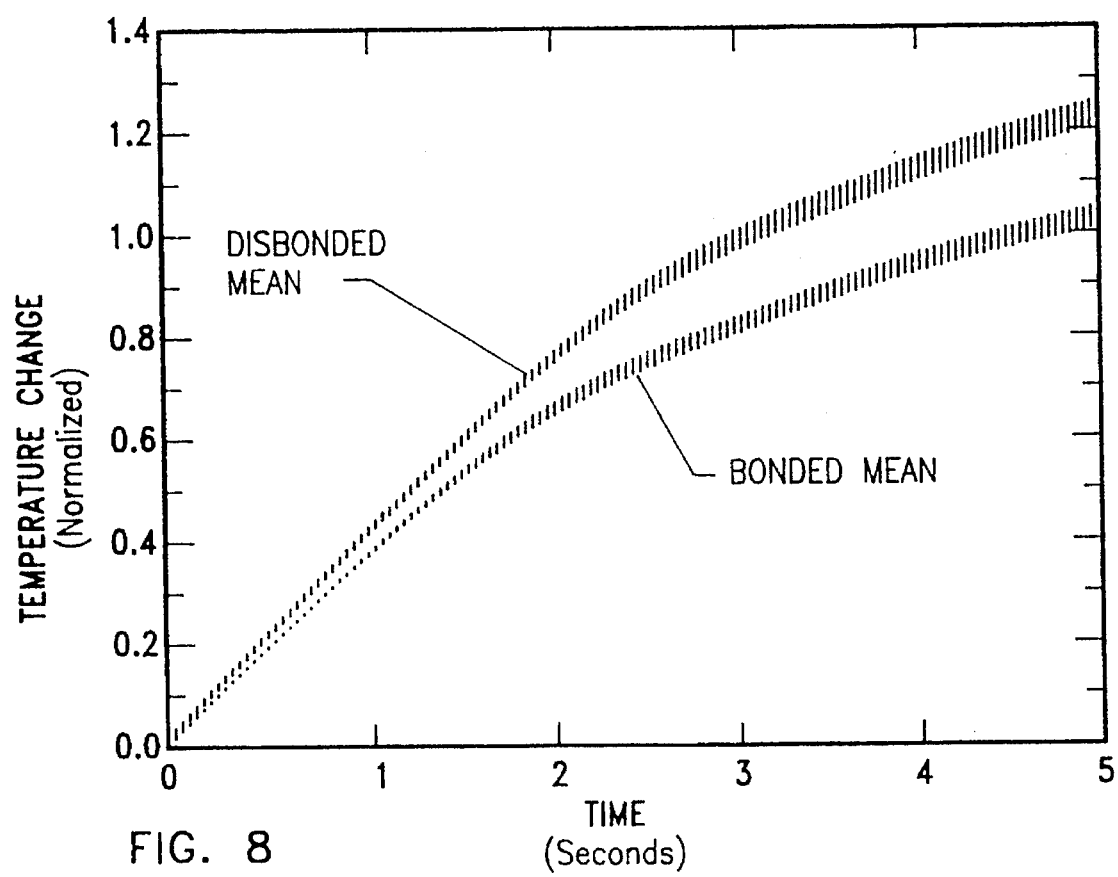
FIG. 8 graphs the mean value of twenty measurements taken of each region of the sample of FIG. 7.

FIG. 8 shows the mean value of twenty measurements taken on the sample over the course of approximately three hours. Measurements were randomly alternated between bonded and disbonded regions. The error bars indicated one standard deviation from the mean. Further analysis indicates that after three seconds the difference between the two measurements is greater than two standard deviations. Therefore there is less than a 5% probability of mistaken identification of bonding in that region.

Figure 9:
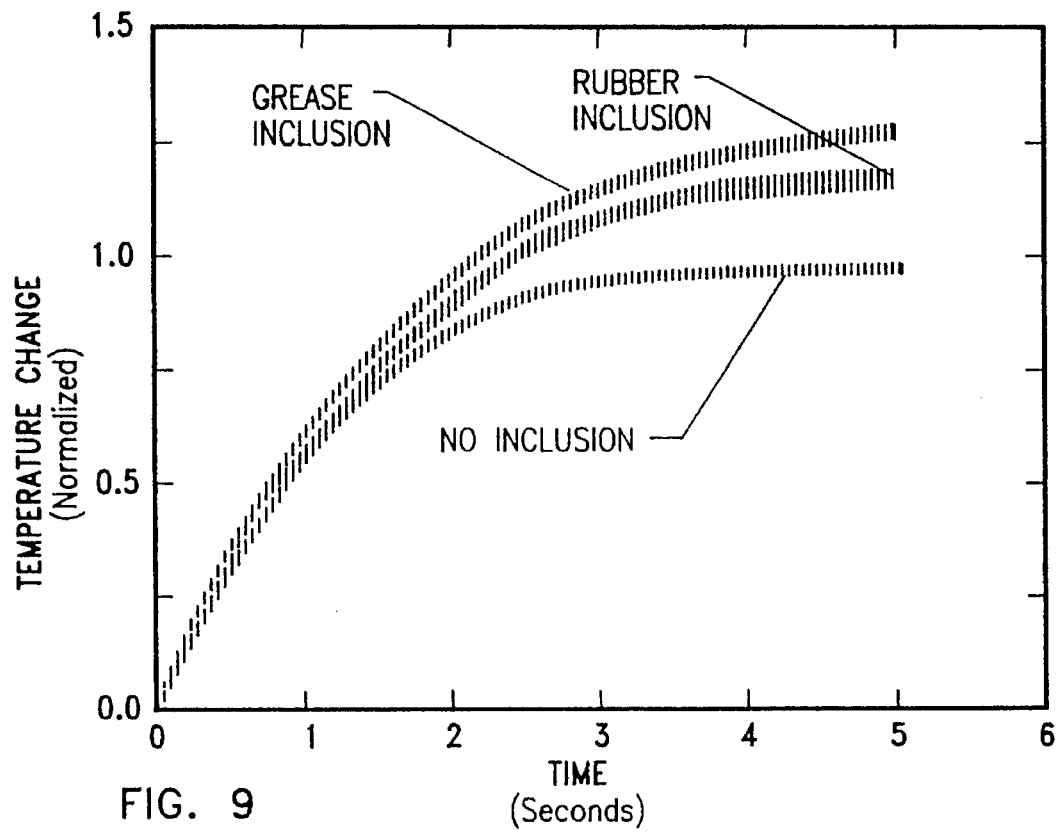
FIG. 9 graphs the normalized temperature change over time for a graphite-epoxy composite sample having a no inclusion region, a rubber inclusion region, and a grease inclusion region located in the sample midplane.

Another sample which was examined was a graphite-epoxy composite. This 16-ply composite sample was manufactured with various midplane inclusions between the eighth and ninth plies. This 30.48 cm square composite had plies laid up at 0°, +45°, −45°, and 90°. Measurements were made over three regions. The first was a region of no inclusion. The second was over a region containing a rubber inclusion. The last was over a region where silicon grease was included between the plies. FIG. 9 shows the results of these measurements. Again data was collected for five seconds with the pyroelectric thermal sensor 16 at a sampling rate of 1.7 KHz with twenty samples being averaged. As can be seen, the regions of inclusion are clearly distinguishable from the fully bonded region, having greater temperature changes than a no inclusion region over the same period. Further there is some separation between the two types of inclusions, though slight because of the similarity in thermal properties between the grease and the rubber.

The injection of heat into the surface of a laminated structure with a disbond results in a surface temperature profile which increases in the region of disbond. By heating over only a small region of the surface and then recording the rate of temperature change at the center of the heating area, a determination of the bond integrity of the laminate at that location can be made.

An investigation of this technique for disbond detection was done by computational simulation of the thermographic technique. A finite element heat transfer algorithm developed at Lawrence Livermore National Laboratory and described by Arthur Shapiro in "TOPAZ2D-A Two-Dimensional Finite Element Code for Heat Transfer Analysis, Electrostatics, and Magnetostatics Problems," UCID-20824, Lawrence Livermore National Laboratory, Livermore, Calif. 94550, July, 1986, was used to mode the three-layer laminated structure. The laminated sample was constructed with a 0.16 cm thick front surface of steel, bonded to a 0.318 cm thick layer of rubber, finally bonded to a 2.54 cm thick layer of aluminum. This sample was 19.0 cm square. A two-dimensional simulation was performed on this sample configuration using a 25×25 element grid clustered around the disbond where the temperature gradients are the largest. The clustering was done using a hyperbolic sine transformation equation, described by Patricia H. James, Christopher S. Welch, William P. Winfree in "A Numerical Grid Generation Scheme for Thermal Simulations in Laminated Structures," *Review of Progress in Quantitative Nondestructive Evaluation*, Vol. 8A, Plenum Publishing Corp., New York, N. Y., 1989, pp. 801–809. The front sudace boundary condition was flux heating and convective cooling.

The output of the finite element model gives the surface temperature of the sample as a fundion of time. To determine the response of the system of interest, this time evolution must be convolved with the response of the detector.

Figure 10:
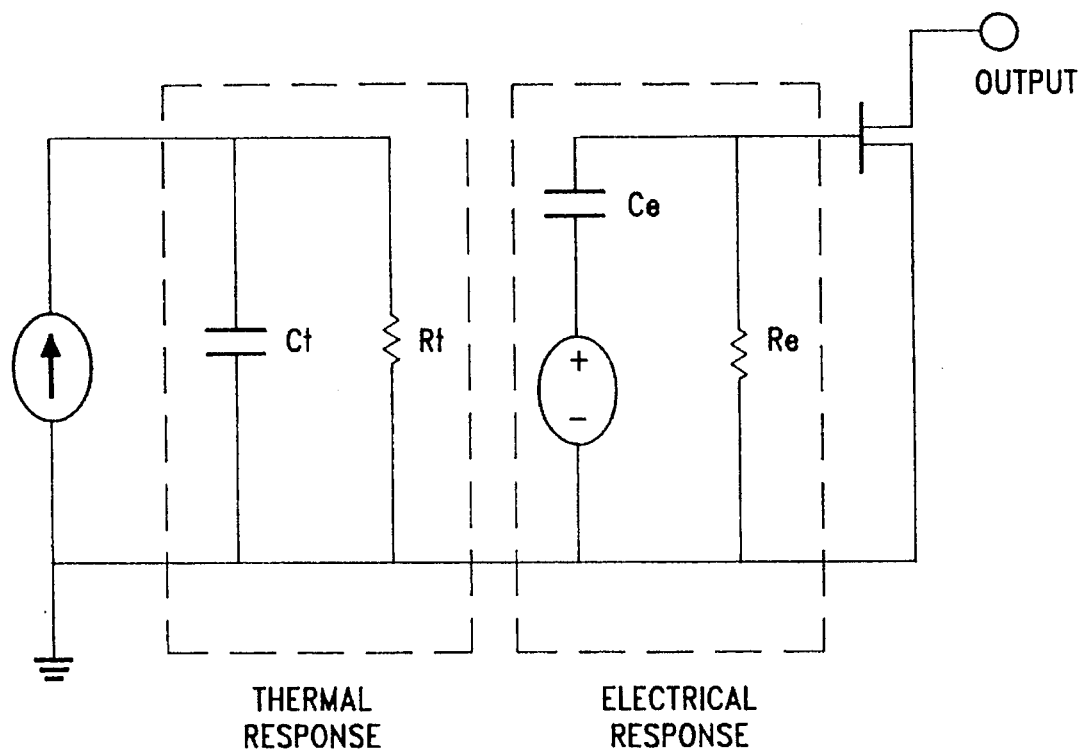
FIG. 10 is an electrical analog circuit for the pyroelectric detector used as a thermal sensor of the thermographic disbond detection system of the present invention.

As a pyroelectric detector, the thermal sensor is sensitive to variations in temperature. The response of the detector is a fundion of both its thermal and electrical responses. These contributions are shown in an electrical analog equivalent circuit for the detector depicted in FIG. 10.

The electrical response is due to the physical capacitance of the sensor element and the internal resistance provided by the manufacturer for coupling to the input of the FET preamplifier. A potential difference arises across the detector element when a temperature differential is present. This electrical response can be thought of as a high pass filter with a time constant $\tau_1$ equal to $R_e C_e$ in the equivalent circuit. The output of such a filter to some arbitrary input wave $V_i(t)$ is given by:

$$V_{Oe}(t) = V_i(t) - V_i(0)e^{-(\frac{t}{\tau_1})} - \frac{1}{\tau_i} \int_0^t V_i(t-\tau)e^{-(\frac{\tau}{\tau_1})} d\tau, \tag{1}$$

where the input voltage $V_i(t)$ is in reality the surface temperature of the sample viewed by the detector.

The second component of the thermal sensor response is thermal in nature. It arises from the physical properties of the detector element. This thermal response is analogous to a low pass filter, providing some maximum rate of temperature change that the detector can respond to. As was done with the electrical response, the response of the thermal component can be expressed as $$V_O(t) = V_{Oe}(0)e^{-(\frac{t}{\tau_2})} - \left(\frac{1}{\tau_2}\right) \int_0^t V_{Oe}(t-\tau)e^{-(\frac{\tau}{\tau_2})} d\tau \tag{2}$$

where $\tau_2$ is the time constant for the low pass filter and equal to $R_t C_t$ in the equivalent circuit. The input function $V_{Oe}(t)$ is the output of the electrical response component given by equation (1).

Equations (1) and (2) can be evaluated numerically quite easily for some discrete set of points $V_i(t)$. The points used for the input would be the time history of the surface temperature as calculated by the finite element model.

Before the thermal sensor response can be calculated, it is necessary to determine the time constants for each component of the response. This was done experimentally. A mechanical shutter was placed between the detector and a blackbody source. The shutter was opened for five seconds, and the output of the detector was measured. These measurements were normalized to give a maximum output of 1. These normalized measurements were compared to a simulation of the response of the detector by sequentially applying equations (1) and (2) to a five seconds square pulse input with an amplitude fixed to give a maximum detector response of 1. The time constants ($\tau_1$ and $\tau_2$) were varied to locate a minimum squared deviation between the simulated and measured response of the detector.

Figure 11:
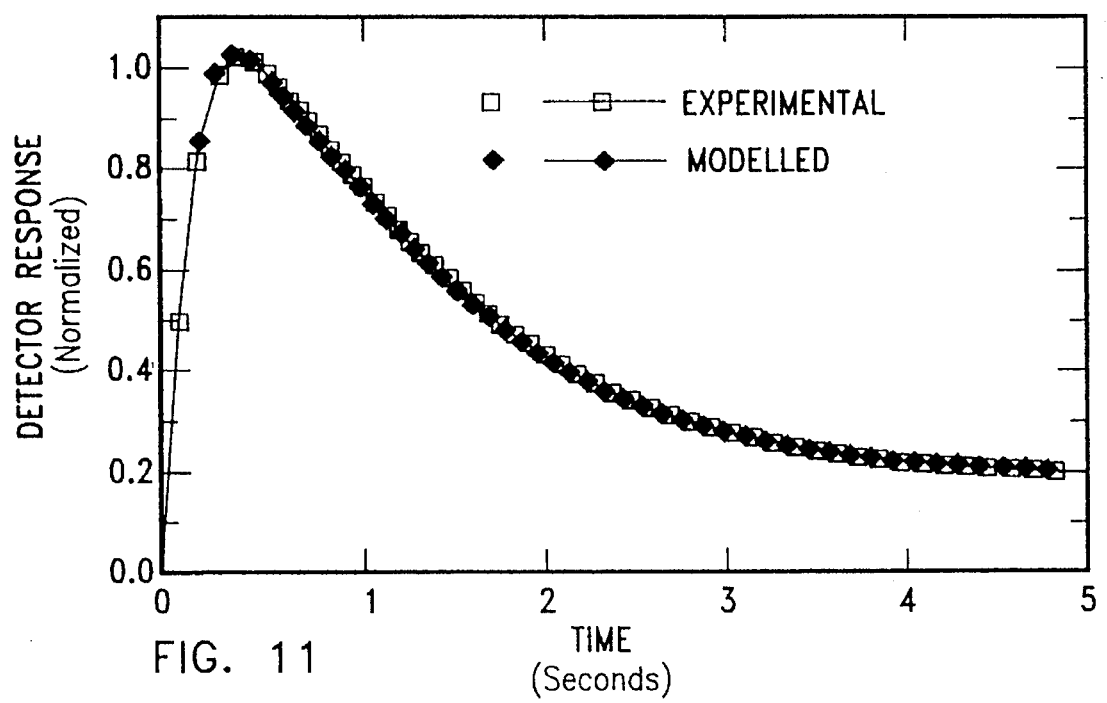
FIG. 11 graphs the modeled and experimental normalized response over time of the pyroelectric detector of FIG. 10.

A comparison of the simulation response with the minimum squared deviation and measured response of the thermal sensor is shown in FIG. 11. The electrical and thermal time constants determined for this simulation are 2.32 and 0.15 seconds respectively. These values fall within the range cited by the manufacturer Microwatt Applications of the thermal sensor.

Two finite element simulations were then performed-one with heating over the disbonded region of the model, the second with heating over a bonded region. The results of each of these runs were then convolved with the simulated detector response. The sample used was the steel-rubber-aluminum laminate described above.

Figure 12:
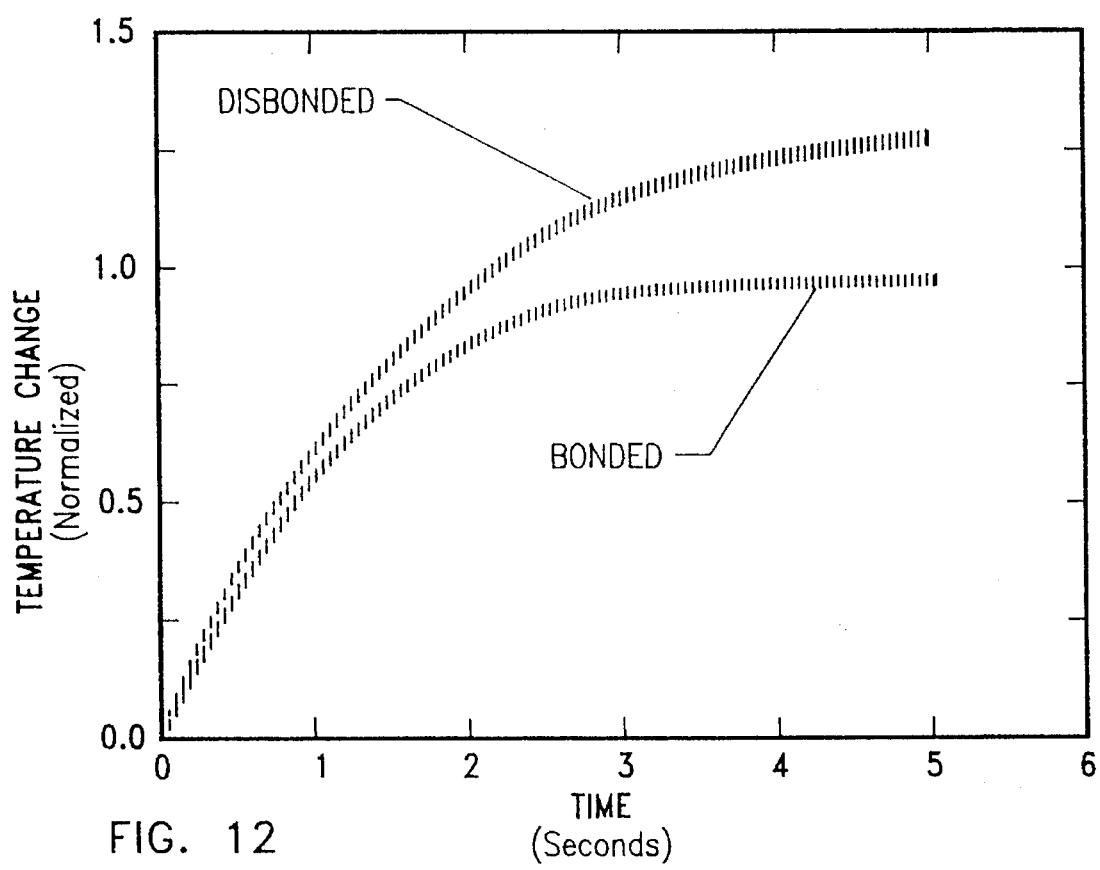
FIG. 12 graphs the normalized temperature change over time for a numerical simulation of the sample of FIG. 7.

FIG. 12 shows the simulation results for both simulation runs. The model results have been normalized to the maximum temperature change for the bonded region. As can be seen from a comparison of this figure to FIG. 7, the numerical simulations agree with the experimental results. The average deviation of the experimental results from the numerical simulations is approximately four percent of the full scale normalized response.

The requirements and responses for a prototype thermal detection system have been presented. This system has been shown to detect the presence of subsurface disbonds in laminated structures. This detection has been shown by statistical analysis to be at least 95% accurate. Application has been shown to both multilayered laminates and to composite structures. Further, an analysis method has been presented for modeling the response of the detector, thus allowing comparison of the experimental results with results from numerical simulations. This comparison shows good agreement thus verifying the technique used by the system.

Calibration standards are determined by generating data curves as discussed in reference to FIGS. 7–9, 11 and 12, i.e., are either experimentally determined or numerically simulated for a laminate sample having a known construction and disbond geography and/or inclusion geography. A test laminate structure is then tested as described above and the obtained temperature changes over time are correlated with the previously determined calibration standards, whereby the disbond and/or inclusion geography of the test structure are determined. All necessary calculations and comparisons can be performed by the personal computer. The particular program employed can either display a quantitative number on the digital display indicative of disbond(s) and/or inclusion(s), e.g., "100" indicating a complete disbond/inclusion of the region at the depth of interest and "0" indicating a good bond with intermediate values indicating corresponding intermediate conditions, or display a specific conclusion based on the quantitative assessment of the sensed temperature changes, e.g., "satisfactory" or "unsatisfactory", "disbonded" or "bonded", "further testing", etc.

Many modifications, improvements and substitutions will be apparent to the skilled artisan without departing from the spirit and scope of the present invention as described herein and defined in the following claims.

We claim:

1. A thermographic detection system for quantitatively analyzing a structure comprising:

a remotely located magnetic induction heating source which generates eddy currents in the structure for heating a region of the structure;

a plurality of thermal sensors arranged along a desired line for sensing temperature changes in the heated region of the structure over time along the desired line, said thermal sensors simultaneously sensing temperature at a single measurement instant; and a computer for assessing the sensed temperature changes quantitatively as a function of time wherein said computer compares the temperature changes sensed in the heated region of the structure with previously determined temperature changes of a calibration sample having known disbond and inclusion characteristics to indicate disbonds and inclusion characteristics of the structure.

2. The thermographic detection system according to claim 1, further comprising an additional thermal sensor arranged non-linearly with respect to said plurality of thermal sensors.

3. The thermographic detection system according to claim 1, wherein each of said plurality of thermal sensors is a pyroelectric detector.

4. The thermographic detection system according to claim 1, further comprising a display which displays the assessed temperature changes.

5. The thermographic detection system according to claim 4, wherein said display displays a numerical value indicative of the disbond and inclusion characteristics of the structure.

6. The thermographic detection system according to claim 4, wherein said display displays a written description indicative of the disbond and inclusion characteristics of the structure.

7. The thermographic detection system according to claim 1, wherein the computer produces a numerical value indicative of the disbond and inclusion characteristics of the structure.

8. The thermographic detection system according to claim 1, wherein the computer produces a written description indicative of the disbond and inclusion characteristics of the structure.

* * * * *

UNITED STATES PATENT AND TRADEMARK OFFICE
CERTIFICATE OF CORRECTION

PATENT NO. : 5,562,345
DATED : October 8, 1996
INVENTOR(S) : Joseph S. Heyman, et al It is certified that error appears in the above-indentified patent and that said Letters Patent is hereby corrected as shown below:

On the title page, item [75]:

Please correct the spelling of the fourth listed inventor's last name to read
----Zalameda---

Signed and Sealed this

Fourteenth Day of January, 1997

Attest:

BRUCE LEHMAN

Attesting Officer     Commissioner of Patents and Trademarks